United States Patent

Leppard et al.

Patent Number: 6,020,528
Date of Patent: *Feb. 1, 2000

[54] ALKYLPHENYLBISACYLPHOSPHINE OXIDES AND PHOTOINITIATOR MIXTURES

[75] Inventors: David George Leppard, Marly, Switzerland; Manfred Köhler, Freiburg; Andreas Valet, Binzen, both of Germany

[73] Assignee: Ciba Specialty Chemicals Corporation, Tarrytown, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/806,498

[22] Filed: Feb. 26, 1997

[30] Foreign Application Priority Data

Mar. 4, 1996 [CH] Switzerland ............... 558/96

[51] Int. Cl.[7] ...................................... C07F 9/53
[52] U.S. Cl. .................. 568/15; 568/16; 568/17
[58] Field of Search ................. 568/15, 16, 17; 522/64

[56] References Cited

U.S. PATENT DOCUMENTS

| | | | |
|---|---|---|---|
| 4,792,632 | 12/1988 | Ellrich ........................................ | 568/15 |
| 4,868,091 | 9/1989 | Boettcher et al. ....................... | 430/281 |
| 4,962,144 | 10/1990 | Babillis et al. . | |
| 5,100,929 | 3/1992 | Jochum ..................... | 522/64 |
| 5,218,009 | 6/1993 | Rutsch ..................... | 522/16 |
| 5,534,559 | 7/1996 | Leppard ..................... | 522/64 |

FOREIGN PATENT DOCUMENTS

| | | |
|---|---|---|
| 0184095 | 6/1986 | European Pat. Off. . |
| 46175 | 2/1991 | European Pat. Off. . |
| 0446175 | 9/1991 | European Pat. Off. . |
| 615980 | 3/1994 | European Pat. Off. . |
| 0551608B1 | 4/1998 | European Pat. Off. . |
| 2259704 | 3/1993 | United Kingdom . |

OTHER PUBLICATIONS

Derwent Abst. 91–269010/37 english trans abst of EP0446175 (1988).
Standard Test Method for Yellowness Index of Plastics ASTM Designation: D 1925—70.

Primary Examiner—Gary Geist
Assistant Examiner—Jean F Vollano
Attorney, Agent, or Firm—Luther A. R. Hall; David R. Crichton

[57] ABSTRACT

Compounds of the formula I

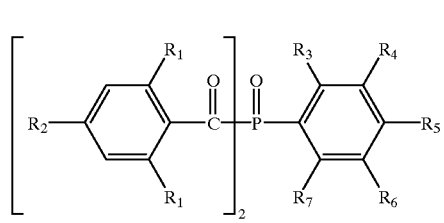

in which $R_1$ is $C_1$–$C_4$alkyl, $R_2$ is hydrogen, $C_1$–$C_4$alkyl or $C_1$–$C_4$alkoxy and $R_3$, $R_4$, $R_5$, $R_6$ and $R_7$ independently of one another are hydrogen, halogen, $C_1$–$C_{20}$alkyl, cyclopentyl, cyclohexyl, $C_2$–$C_{12}$alkenyl, $C_2$–$C_{18}$alkyl which is interrupted by one or more oxygen atoms, or are phenyl-substituted $C_1$–$C_4$alkyl, or are phenyl which is unsubstituted or is mono- or disubstituted by $C_1$–$C_4$alkyl and/or $C_1$–$C_4$alkoxy with the provisos that at least one of the radicals $R_3$, $R_4$, $R_5$, $R_6$ and $R_7$ is other than hydrogen and that, if $R_1$ and $R_2$ are methyl, $R_3$ and $R_6$ are not methyl, and mixtures of such compounds with α-hydroxy ketones, benzophenones and α-amino ketones, are suitable as photoinitiators.

5 Claims, No Drawings

ALKYLPHENYLBISACYLPHOSPHINE OXIDES AND PHOTOINITIATOR MIXTURES

The invention relates to alkylphenylbisacylphosphine oxides and to specific mixtures of bisacylphosphine oxide compounds with other photoinitiators.

Bisacylphosphine oxide compounds are known as photoinitiators from EP-A-184095, for example. Alkylbisacylphosphine oxides and also mixtures of these compounds with α-hydroxy ketones or benzophenone compounds are disclosed in GB-A-2259704. EP-A-446175 describes mixtures of three components, namely mono- or bisacylphosphine oxide, α-hydroxyketone and benzophenone.

In industry there is a need for effective photoinitiators and photoinitiator mixtures which are capable of curing photopolymerizable compositions efficiently and without extreme yellowing phenomena.

It has now been found that compounds of the formula I

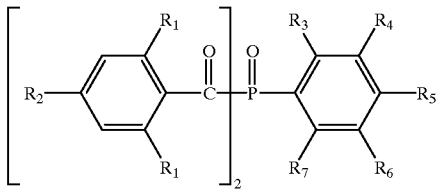

(I)

in which $R_1$ is $C_1$–$C_4$alkyl, $R_2$ is hydrogen, $C_1$–$C_4$alkyl or $C_1$–$C_4$alkoxy and $R_3$, $R_4$, $R_5$, $R_6$ and $R_7$ independently of one another are hydrogen, halogen, $C_1$–$C_{20}$alkyl, cyclopentyl, cyclohexyl, $C_2$–$C_{12}$alkenyl, $C_2$–$C_{18}$alkyl which is interrupted by one or more oxygen atoms, or are phenyl-substituted $C_1$–$C_4$alkyl, or are phenyl which is unsubstituted or is mono- or disubstituted by $C_1$–$C_4$alkyl and/or $C_1$–$C_4$alkoxy, with the provisos that at least one of the radicals $R_3$, $R_4$, $R_5$, $R_6$ and $R_7$ is other than hydrogen and that, if $R_1$ and $R_2$ are methyl, $R_3$ and $R_6$ are not methyl, are suitable as very good photoinitiators.

It has also been found that the photoinitiators of the formula 1a can be combined with compounds of the formula II, III and/or IV to give initiator mixtures (blends) having good curing properties, especially in respect of the required surface curing and through-curing of polymerizable compositions. The cured compositions, moreover, exhibit highly advantageous properties in the context of yellowing. This application therefore provides a photoinitiator mixture comprising at least one compound of the formula (1a)

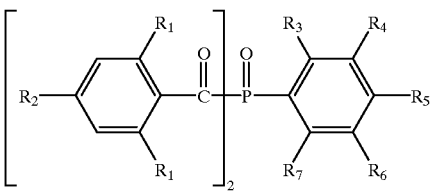

(Ia)

in which $R_1$ is $C_1$–$C_4$alkyl;

$R_2$ is hydrogen, $C_1$–$C_4$alkyl or $C_1$–$C_4$alkoxy, and $R_3$, $R_4$, $R_5$, $R_6$ and $R_7$ independently of one another are hydrogen, halogen, $C_1$–$C_{20}$alkyl, cyclopentyl, cyclohexyl, $C_2$–$C_{12}$alkenyl, $C_2$–$C_{18}$alkyl which is interrupted by one or more oxygen atoms, or are phenyl-substituted $C_1$–$C_4$alkyl, or are phenyl which is unsubstituted or is mono- or disubstituted by $C_1$–$C_4$alkyl and/or $C_1$–$C_4$alkoxy; and at least one compound of the formula (II)

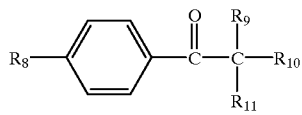

(II)

in which $R_8$ is hydrogen, $C_1$–$C_{18}$alkyl, $C_1$–$C_{18}$alkoxy, —OCH$_2$CH$_2$—OR$_{12}$, a group

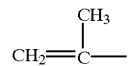

or a group

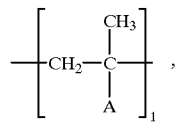

in which l is a number from 2 to 10 and A is a radical

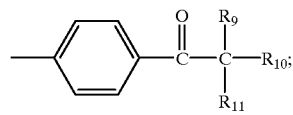

$R_9$ and $R_{10}$ independently of one another are hydrogen, $C_1$–$C_6$alkyl, phenyl, $C_1$–$C_{16}$-alkoxy, OSiR$_{13}$R$_{14}$R$_{14a}$ or —O(CH$_2$CH$_2$O)$_q$—C$_1$–C$_{16}$alkyl, in which q is a number from 1 to 20, or $R_9$ and $R_{10}$, together with the carbon atom to which they are attached, form a cyclohexyl ring;

$R_{11}$ is hydroxyl, $C_1$–$C_{16}$alkoxy or —O(CH$_2$CH$_2$O)$_q$—C$_1$–C$_{16}$alkyl;

where $R_9$, $R_{10}$ and $R_{11}$ are not all simultaneously $C_1$–$C_{16}$alkoxy or —O(CH$_2$CH$_2$O)$_q$—C$_1$–C$_{16}$alkyl, $R_{12}$ is hydrogen, $C_1$–$C_8$alkyl,

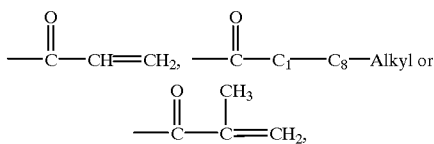

and $R_{13}$, $R_{14a}$ and $R_{14}$ independently of one another are $C_1$–$C_4$alkyl or phenyl; and/or at least one compound of the formula (III)

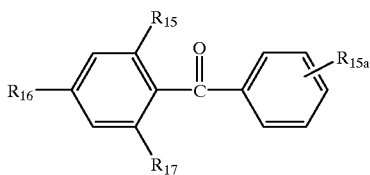
(III)

in which

R$_{15}$, R$_{15a}$, R$_{16}$ and R$_{17}$ independently of one another are hydrogen, methyl, phenyl, methoxy, —COOH, unsubstituted or C$_1$–C$_4$alkyl-substituted phenyl, or a group —OCH$_2$CH$_2$OR$_{12}$ or —SCH$_2$CH$_2$OR$_{12}$ in which R$_{12}$ is as defined for formula II; and/or at least one compound of the formula (IV)

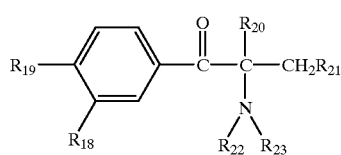
(IV)

in which

R$_{18}$ is hydrogen, C$_1$–C$_4$alkyl, C$_1$–C$_4$alkoxy, C$_1$–C$_4$alkylthio, halogen or a group N(R$_{22}$)$_2$;

R$_{19}$ is as defined for R$_{18}$ or is the group

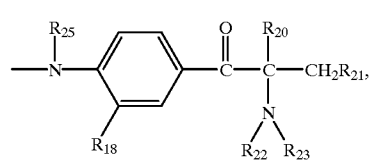
(IVa)

in which case the radical R$_{18}$ from the formula IV and the radical R$_{18}$ of this group (IVa) together are a direct bond, and the other radicals are as defined below;

R$_{20}$ is C$_1$–C$_8$alkyl;

R$_{21}$ is hydrogen, —CH=CHR$_{24}$, or phenyl which is unsubstituted or is substituted one to three times by C$_1$–C$_{12}$alkyl, C$_1$–C$_4$alkoxy or halogen;

or R$_{20}$ and R$_{21}$, together with the carbon atom to which they are attached, form a cyclohexyl ring;

R$_{22}$ and R$_{23}$ independently of one another are C$_1$–C$_4$alkyl, or

R$_{22}$ and R$_{23}$, together with the nitrogen atom to which they are attached, form a five- or six-membered saturated or unsaturated ring which can be interrupted by —O—, —NH— or —N(CH$_3$)—, R$_{24}$ is hydrogen or C$_1$–C$_4$alkyl; and R$_{25}$ is hydrogen or C$_1$–C$_{12}$alkyl.

C$_1$–C$_{20}$alkyl can be linear or branched and is, for example, methyl, ethyl, propyl, isopropyl, butyl, isobutyl, sec-butyl, tert-butyl, pentyl, isopentyl, hexyl, heptyl, octyl, nonyl, decyl, dodecyl, octadecyl or eicosyl. Preference is given to C$_1$–C$_{18}$alkyl, e.g. C$_1$–C$_{12}$- or C$_1$–C$_8$alkyl, especially C$_1$–C$_4$alkyl.

C$_1$–C$_{18}$alkyl, C$_1$–C$_6$alkyl and C$_1$–C$_4$alkyl can have the same meanings as given above up to the corresponding number of carbon atoms.

C$_2$–C$_{18}$alkyl interrupted by one or more oxygen atoms is, for example, interrupted by 1 5, e.g. 1–3 or 1 or 2 times by —O—. This produces structural units such as —O(CH$_2$)$_2$OH, —O(CH$_2$)$_2$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]$_y$—CH$_3$, where y=1–5,—(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

The radical —O(CH$_2$CH$_2$O)$_q$—C$_1$–C$_{16}$alkyl represents 1 to 20 successive ethylene oxide units whose chain ends in a C$_1$–C$_{16}$alkyl. q is preferably q 1 to 10, e.g. 1 to 8, especially 1 to 6. The chain of ethylene oxide units ends in a C$_1$–C$_{12}$alkyl, e.g. C$_1$–C$_8$alkyl, in particular in a C$_1$–C$_4$alkyl. Here C$_1$–C$_{16}$alkyl can have the meanings given above up to the corresponding number of carbon atoms.

C$_2$–C$_{12}$alkenyl can be linear or branched and there may be more than one unsaturated bond in the molecule. Examples are vinyl, allyl, methylvinyl, butenyl, pentenyl, hexenyl, heptenyl, octenyl, nonenyl, decenyl, dodecenyl.

C$_1$–C$_{18}$alkoxy can be linear or branched and is, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, decyloxy, dodecyloxy or octadecyloxy. Further examples are C$_1$–C$_{12}$alkoxy or C$_1$–C$_8$alkoxy, especially C$_1$–C$_4$alkoxy.

C$_1$–C$_6$alkoxy and C$_1$–C$_4$alkoxy can have the same meanings as given above up to the corresponding number of carbon atoms.

C$_1$–C$_4$alkylthio can be linear or branched and is, for example, methylthio, ethylthio, propylthio, isopropylthio, butylthio or tert-butylthio, especially methylthio.

Phenyl-substituted C$_1$–C$_4$alkyl is, for example, benzyl, 2-phenylethyl, 3-phenylpropyl, α-methylbenzyl or α,α-dimethylbenzyl, especially benzyl.

Substituted phenyl is substituted from one to five times, for example once, twice or three times, especially once or twice, on the phenyl ring. The pattern of substitution on the phenyl ring is, for example, 2-, 3-, 4-, 5-, 2,4-, 2,5-, 2,6-, 3,4-, 3,5-, 2,4,6- or 3,4,5-. C$_1$–C$_4$alkyl and C$_1$–C$_4$alkoxy substituents can have the meanings given above. Examples of substituted phenyl are tolyl, xylyl, 4-methoxyphenyl, 2,4-and 2,5-dimethoxyphenyl, ethylphenyl, and 4-alkoxy-2-methylphenyl.

Halogen is, for example, chlorine, bromine or iodine, especially chlorine.

If R$_{19}$ is the group

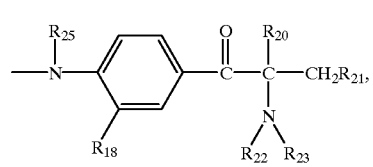
(IVa)

where the radical R$_{18}$ from the formula IV and the radical R$_{18}$ of this group together are a direct bond, then the result is structures of the formula IVb

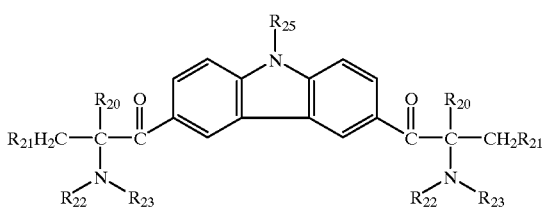

If $R_{22}$ and $R_{23}$, together with the nitrogen atom to which they are attached, form a ring which can additionally be interrupted by —O—, —NH— or —N(CH$_3$)—, then the ring formed is, for example, a morpholino, piperidino or methylpiperidino ring.

The novel compounds of the formula I (and 1a) can be prepared, for example, by double acylation of a primary phosphine (V) with at least 2 equivalents of an acid chloride (VI) in the presence of at least two equivalents of a base and subsequent oxidation of the resulting diacylphosphine (VII) in accordance with the equations:

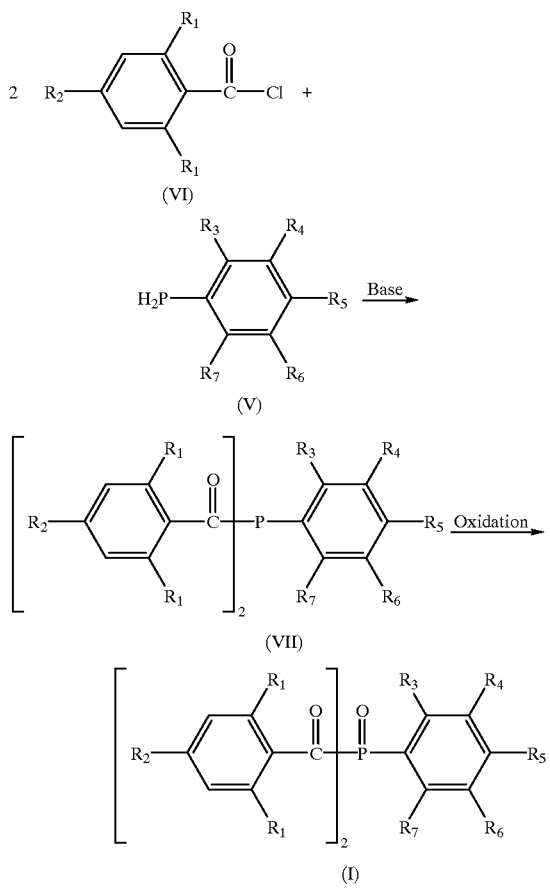

$R_1$, $R_2$, $R_3$, $R_4$, $R_5$, $R_6$ and $R_7$ are as defined in claim 8.

Examples of suitable bases are tertiary amines, pyridine, alkali metals, lithium diisopropylamide, butyllithium, alkaline earth metal carbonates, alkali metal alcoholates and alkali metal hydrides. The first reaction stage takes place preferably in solution. Particularly suitable solvents are hydrocarbons, such as alkanes and alkane mixtures, cyclohexane, benzene, toluene and xylene. The reaction is carried out at various temperatures depending on the solvent and starting materials used. In the case of the use of bases such as lithium diisopropylamide or butyllithium, it is expedient to work, for example, at from −40 to 0° C.

Reactions using tertiary amines, alkali metals or alkali metal hydrides as bases are expediently carried out, for example, at from 10 to 120° C., preferably from 20 to 80° C. After the base chloride formed has been separated off, the phosphine (VII) can be isolated by evaporative concentration. The crude reaction product can be used further without purification or else can be purified by means, for example, of crystallization. However, the second reaction stage can also be carried out without isolating (VII), using the solution of the crude product.

Particularly suitable oxidizing agents for the second stage in the preparation of the oxides are hydrogen peroxide and organic peroxy compounds, examples being peracetic acid, air and pure oxygen.

The reaction products can be purified by conventional methods, for example by crystallization or chromatography.

The phosphines of the formula (V) can be prepared, for example, by reducing the corresponding dichlorides (VIII), phosphonic esters (IX) or phosphonous esters (X):

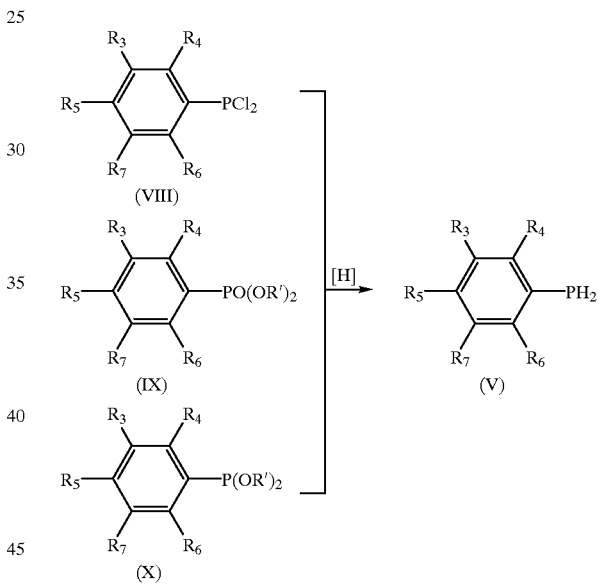

R′ is, for example, methyl or ethyl.

Reductions are usually carried out with LiAlH$_4$; SiHCl$_3$; Ph$_2$SiH$_2$; a) LiH b) H$_2$O;

a) Li/tetrahydrofuran b) H$_2$O or a) Na/toluene b) H$_2$O.

Hydrogenation using LiAlH$_4$, for example, can also be found in Helv. Chim. Acta 1966, No. 96, page 842.

The dichlorophosphine compounds of the formula VIII can be obtained, for example, by reacting a corresponding aromatic compound with phosphorus trichloride and aluminium chloride.

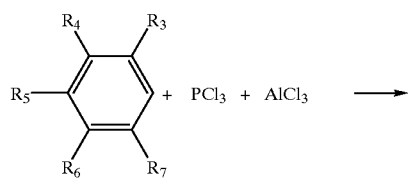

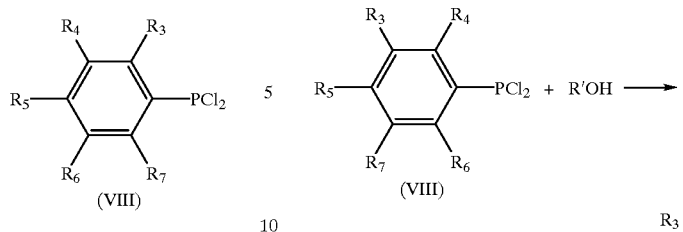

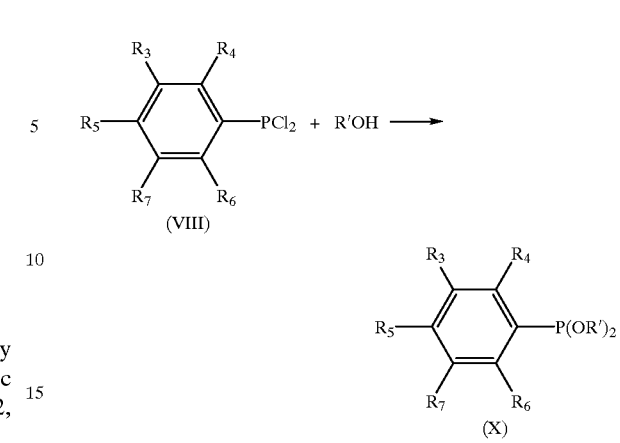

The dichlorides (VIII) can also be obtained, for example, by Grignard reaction of the corresponding brominated aromatic compounds (XI) with $PCl_3$ (cf. e.g. Helv.Chim. Acta 1952, No 35, page 1412):

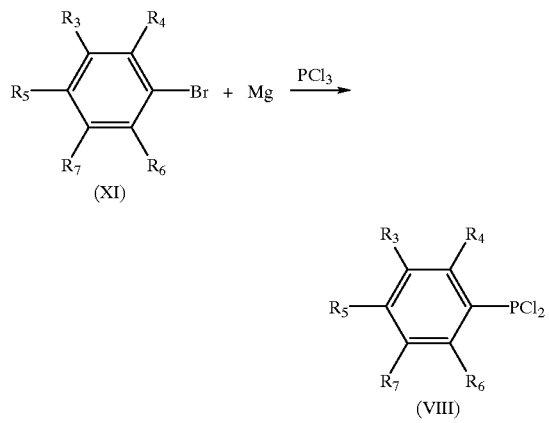

$R_1$, $R_2$ $R_3$, $R_4$, $R_5$, $R_6$ and $R_7$ are as defined in claim 8.

The diesters of formula (IX) can be prepared, for example, by reacting the brominated aromatic compounds (XI) with a trisphosphorous ester (XII). Reactions of this kind are described, for example in DE-C-1810431.

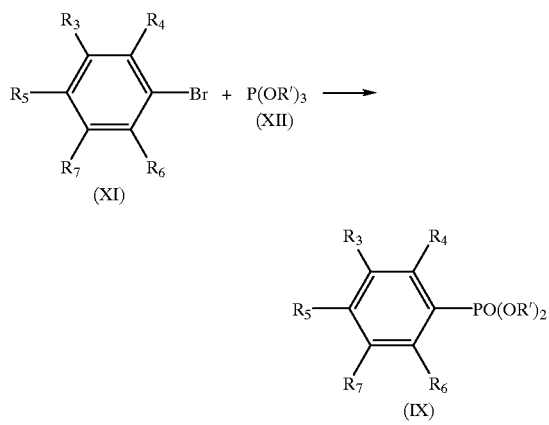

The phosphonous esters (X) can be obtained, for example by reacting a phosphorus dichloride (VIII) with an alcohol:

The brominated aromatic compounds (XI) are obtained by prior-art bromination reactions, for example by reacting alkoxylated aromatic compounds with N-bromosuccinimide or bromine/acetic acid.

The acid chlorides of the formula (VI) are prepared by generally known methods from the prior art.

The preparation of the compounds of the formulae II and III is generally known, and some of the compounds are commercially available. The preparation of oligomeric compounds of the formula II, for example, is described in EP-A-161 463. A description of the preparation of the compounds of the formula III can be found for example in EP-A-209 831. The preparation of compounds of the formula IV is given, for example, in EP-A-3002 or EP-A-284 561. Furthermore, some compounds of the formula IV are available commercially.

Examples of novel compounds are:
Bis(2,4,6-trimethylbenzoyl)-2,5-diisopropylphenylphosphine oxide;
bis(2,4,6-trimethylbenzoyl)-2-methylphenylphosphine oxide;
bis(2,4,6-trimethylbenzoyl)-4-methylphenylphosphine oxide;
bis(2,4,6-trimethylbenzoyl)-2,5-diethylphenylphosphine oxide;
bis(2,4,6-trimethylbenzoyl)-2,3,5,6-tetramethylphenylphosphine oxide.

The novel photoinitiator mixtures are prepared, for example, by mixing, milling, melting or dissolving the individual components, it being possible to use liquid components as solvents for the respective combination partners. It is also possible, however, to combine the components in an inert solvent.

The photoinitiator mixtures comprise, for example, 2–90%, e.g. 5–50%, 5–40%, especially 5–25%, of compounds of formula Ia and 98–50%, e.g. 95–60%, especially 95–75%, of compounds of the formula II, III and/or IV. Other mixtures which are of interest are those in which the proportion of compounds of the formula Ia in the mixture with compounds of the formula II and III and/or IV is from 30 to 70%.

Preferred examples of compounds of the formula II and III are
1-benzoylcyclohexanol, 2,2-dimethoxy-1,2-diphenylethan-1-one and 1-benzoyl-1-hydroxy-1-methylethane.

Examples of novel photoinitiator mixtures (blends) are
5% bis(2,4,6-trimethylbenzoyl)phenylphosphine oxide and 95% 1-benzoyl-1-hydroxy-1-methylethane;

5% bis(2,4,6-trimethylbenzoyl)phenylphosphine oxide and 95% 1-benzoylcyclohexanol;
25% bis(2,4,6-trimethylbenzoyl)phenylphosphine oxide and 75% 1-benzoylcyclohexanol;
25% bis(2,4,6-trimethylbenzoyl)phenylphosphine oxide and 75% 1-benzoyl-1-hydroxy-1-methylethane;
25% bis(2,4,6-trimethylbenzoyl)phenylphosphine oxide and 75% 2,2-dimethoxy-1,2-diphenylethan-1-one;
5% bis(2,4,6-trimethylbenzoyl)phenylphosphine oxide and 95% 2,2-dimethoxy-1,2-diphenylethan-1-one;
25% bis(2,4,6-trimethylbenzoyl)phenylphosphine oxide and 75% 4-(2-hydroxyethoxy)benzoyl-1-hydroxy-1-methylethane;
5% bis(2,4,6-trimethylbenzoyl)phenylphosphine oxide and 95% 4-(2-hydroxyethoxy)benzoyl-1-hydroxy-1-methylethane;
5% bis(2,4,6-trimethylbenzoyl)-2,5-diisopropylphenylphosphine oxide and 95% 1-benzoylcyclohexanol;
5% bis(2,4,6-trimethylbenzoyl)-2,5-diisopropylphenylphosphine oxide and 95% 1-benzoyl-1-hydroxy-1-methylethane;
25% bis(2,4,6-trimethylbenzoyl)-2,5-diisopropylphenylphosphine oxide and 75% 1-benzoylcyclohexanol;
25% bis(2,4,6-trimethylbenzoyl)-2,5-diisopropylphenylphosphine oxide and 75% 1-benzoyl-1-hydroxy-1-methylethane;
5% bis(2,4,6-trimethylbenzoyl)-4-tert-butyl-2,6-dimethylphenylphosphine oxide and 95% 1-benzoylcyclohexanol;
5% bis(2,4,6-trimethylbenzoyl)-4-tert-butyl-2,6-dimethylphenylphosphine oxide and 95% 1-benzoyl-1-hydroxy-1-methylethane;
25% bis(2,4,6-trimethylbenzoyl)-4-tert-butyl-2,6-dimethylphenylphosphine oxide and 75% 1-benzoylcyclohexanol;
25% bis(2,4,6-trimethylbenzoyl)-4-tert-butyl-2,6-dimethylphenylphosphine oxide and 75% 1-benzoyl-1-hydroxy-1-methylethane;
5% bis(2,6-dimethylbenzoyl)phenylphosphine oxide and 95% 1-benzoyl-1-hydroxy-1-methylethane;
5% bis(2,6-dimethylbenzoyl)phenylphosphine oxide and 95% 1-benzoylcyclohexanol;
25% bis(2,6-dimethylbenzoyl)phenylphosphine oxide and 75% 1-benzoyl-1-hydroxy-1-methylethane;
25% bis(2,6-dimethylbenzoyl)phenylphosphine oxide and 75% 1-benzoylcyclohexanol;
5% bis(2,4,6-trimethylbenzoyl)-2,5-dimethylphenylphosphine oxide and 95% 1-benzoylcyclohexanol;
5% bis(2,4,6-trimethylbenzoyl)-2,5-dimethylphenylphosphine oxide and 95% 1-benzoyl-1-hydroxy-1-methylethane;
25% bis(2,4,6-trimethylbenzoyl)-2,5-dimethylphenylphosphine oxide and 75% 1-benzoylcyclohexanol;
25% bis(2,4,6-trimethylbenzoyl)-2,5-dimethylphenylphosphine oxide and 75% 1-benzoyl-1-hydroxy-1-methylethane;
25% bis(2,4,6-trimethylbenzoyl)-2,5-dimethylphenylphosphine oxide and 75% 2,2-dimethoxy-1,2-diphenylethan-1-one;
25% bis(2,4,6-trimethylbenzoyl)-2,5-dimethylphenylphosphinoxide and 75% 4-(2-hydroxyethoxy)benzoyl-1-hydroxy-1-methylethane.

Photoinitiator mixtures of particular interest are those obtained by dissolving bis(2,4,6-trimethylbenzoyl) phenylphosphine oxide in a liquid hydroxy ketone compound. More than 2 components, especially 3, are preferably used in the mixture. The three-component mixtures are expediently prepared by mixing the respective constituents and heating the mixture gently, for example at 50–60° C.

The invention additionally provides photoinitiator mixtures comprising at least one compound of the formula Ia and two compounds of the formula II.

Preference is given, for example, to 3-component mixtures comprising
25% bis(2,4,6-trimethylbenzoyl)phenylphosphine oxide,
70% 1-benzoylcyclohexanol and
5% 1-benzoyl-1-hydroxy-1-methylethane; or
25% bis(2,4,6-trimethylbenzoyl)phenylphosphine oxide,
60% 1-benzoylcyclohexanol and
15% 1-benzoyl-1-hydroxy-1-methylethane; or
25% bis(2,4,6-trimethylbenzoyl)phenylphosphine oxide,
50% 1-benzoylcyclohexanol and
25% 1-benzoyl-1-hydroxy-1-methylethane.

Preference is given to compounds of the formula I in which $R_3$, $R_4$, $R_5$, $R_6$ and $R_7$ are hydrogen, $C_1$–$C_8$alkyl, phenyl, allyl, benzyl, cyclohexyl or chlorine.

Further advantageous compounds of the formula I and Ia are those in which $_3$, $R_4$ and $R_5$ are hydrogen, $C_1$–$C_4$alkyl, especially methyl, or phenyl.

Attention is drawn to compounds of the formula I and Ia in which $R_6$ and $R_7$ are hydrogen or $C_1$–$C_4$alkyl, especially methyl.

Particular preference is given to those compounds of the formula I and Ia in which $R_2$ is hydrogen or $C_1$–$C_4$alkyl.

Preference extends to the compounds of the formula I and Ia in which $R_1$ is methyl.

Preference is likewise given to compounds of the formula I and Ia in which $R_1$ and $R_2$ are the same.

Also of interest are compounds of the formula I and Ia in which $R_1$ and $R_2$ are $C_1$–$C_4$alkyl, especially methyl.

In the novel photoinitiator mixtures, preference is given to the use of compounds of the formula Ia, in which $R_3$, $R_4$, $R_5$, $R_6$ and $R_7$ are hydrogen.

Further compounds of the formula Ia used with preference are those in which $R_3$ and $R_6$ are methyl.

Other photoinitiator mixtures of interest are those in which, in the compounds of the formula Ia, $R_3$, $R_4$, $R_5$, $R_6$ and $R_7$ are hydrogen.

Further preferred photoinitiator mixtures are those comprising compounds of the formula Ia and compounds of the formula II in which $R_8$ is hydrogen, $C_1$–$C_4$alkyl, $C_1$–$C_4$alkoxy, —OCH$_2$CH$_2$OR$_{12}$, a group

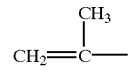

or a group

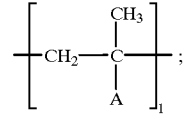

$R_9$ and $R_{10}$ independently of one another are hydrogen, $C_1$–$C_3$alkyl, phenyl, $C_1$–$C_{12}$alkoxy or —O(CH$_2$CH$_2$O)$_q$—$C_1$–$C_8$alkyl in which q is a number from 1 to 10, or $R_9$ and $R_{10}$, together with the carbon atom to which they are attached, form a cyclohexyl ring; $R_{11}$ is hydroxyl, $C_1$–$C_4$alkoxy or —O(CH$_2$CH$_2$O)$_q$—$C_1$–$C_8$alkyl; and/or compounds of the formula III, and/or compounds of the formula IV in which $R_{18}$ is hydrogen or methoxy; $R_{19}$ is methoxy, methylthio, morpholino or a group of the formula IVa; $R_{20}$ is methyl or ethyl; $R_{22}$ and $R_{23}$ are the same and are methyl or, together with the nitrogen atom to which they are attached, form a five- or six-membered saturated ring which can be interrupted by —O—; and $R_{25}$ is hydrogen or $C_1$–$C_8$alkyl.

There is likewise interest in a photoinitiator mixture comprising compounds of the formula II in which $R_8$ is hydrogen, $C_1$–$C_4$alkyl, $C_1$–$C_4$ alkoxy or —$OCH_2CH_2OR_{12}$; $R_9$ and $R_{10}$ independently of one another are hydrogen, phenyl, methyl, or methoxy or $R_9$ and $R_{10}$, together with the carbon atom to which they are attached, form a cyclohexyl ring; and $R_{11}$ is hydroxyl or methoxy.

Other preferred photoinitiator mixtures are those in which the compound of the formula III is benzophenone, 2,4,6-trimethylphenyl phenyl ketone, 4-methylphenyl phenyl ketone, (3-methyl-4-methoxyphenyl 3-methylphenyl ketone, 4-(4-methylphenylthio)phenyl phenyl ketone, 2-carboxyphenyl phenyl ketone or 4-(2-hydroxyethoxy) phenyl phenyl ketone. Also preferred are photoinitiator mixtures in which the compound of the formula II is 1-benzoyl-1-hydroxy-1-methylethane, 1-benzoylcyclohexanol, 4-[(2-hydroxyethoxy)benzoyl]-1-hydroxy-1-methylethane, 1-(4-isopropylbenzoyl)-1-hydroxy-1-methylethane or 2,2-dimethoxy-1,2-diphenylethan-1-one.

Preference extends to photoinitiator mixtures in which the compound of the formula IV is 1-(3,4-dimethoxybenzoyl)-1-benzyl-1-morpholinopropane, 1-(4-methylthiobenzoyl)-1-methyl-1-morpholinoethane, 1-(4-morpholinobenzoyl)-1-benzyl-1-dimethylaminopropane or 3,6-bis(2-methyl-2-morpholinopropan-1-one)-9-octylcarbazole.

Also of interest are photoinitiator mixtures in which the compound of the formula Ia is bis(2,4,6-trimethylbenzoyl)-2,5-diisopropylphenylphosphine oxide, bis[2,6-dimethyl-4-(2-methylpropyl)benzoyl]phenylphosphine oxide, bis(2,6-dimethylbenzoyl)phenylphosphine oxide, bis(2,4,6-trimethylbenzoyl)phenylphosphine oxide or bis(2,4,6-trimethylbenzoyl)-2,5-dimethylphenylphosphine oxide.

The novel photoinitiator mixtures comprise, as compound of the formula Ia, preferably bis(2,4,6-trimethylbenzoyl) phenylphosphine oxide.

Preference is given to mixtures without benzophenone.

Preference is given to mixtures comprising compounds of the formula II.

Also of interest are photoinitiator mixtures comprising, as compound of the formula Ia, bis(2,4,6-trimethylbenzoyl)-2,5-diisopropylphenylphosphine oxide; bis(2,4,6-trimethylbenzoyl)-2-methylphenylphosphine oxide; bis(2,4,6-trimethylbenzoyl)-4-methylphenylphosphine oxide; bis(2,4,6-trimethylbenzoyl)-2,5-diethylphenylphosphine oxide and/or bis(2,4,6-trimethylbenzoyl)-2,3,5,6-tetramethylphenylphosphine oxide.

Particular preference is given to a photoinitiator mixture comprising 25% bis(2,4,6-trimethylbenzoyl) phenylphosphine oxide and 75% 1-benzoylcyclohexanol. Likewise preferred is a photoinitiator mixture comprising 25% bis(2,4,6-trimethylbenzoyl)-phenylphosphine oxide and 75% 1-benzoyl-1-hydroxy-1-methylethane.

Also of interest are photoinitiator mixtures comprising two or more compounds of the formula Ia, or mixtures of compounds of the formula Ia with other bisacylphosphine oxides and/or monoacylphosphine oxides and compounds of the formulae II and/or III, for example a combination of bis (2,4,6-trimethylbenzoyl)-phenylphosphine oxide, bis(2,6-dimethoxybenzoyl)(1,4,4-trimethylpentyl)phosphine oxide, 1-benzoylcyclohexanol or, for example, of bis(2,4,6-trimethylbenzoyl)phenylphosphine oxide, bis(2,6-dimethoxybenzoyl)(1,4,4-trimethylpentyl)phosphinoxide and 1-benzoyl-1-hydroxy-1-methylethane or for example, of bis(2,4,6-trimethylbenzoyl)-phenylphosphine oxide, bis(2,4,6-trimethylbenzoyl)-2,5-dimethylphenylphosphine oxide, 1-benzoyl-1-hydroxy-1-methylethane and/or 1-benzoyl-1-hydroxy-1-methylethane, of bis(2,4,6-trimethylbenzoyl)-phenylphosphine oxide, 2,4,6-trimethylbenzoyldiphenylphosphine oxide, 1-benzoyl-1-hydroxy-1-methylethane and/or 1-benzoyl-1-hydroxy-1-methylethane, or of bis(2,4,6-trimethylbenzoyl)-2,4-dipentoxyphenylphosphine oxide, 1-benzoyl-1-hydroxy-1-methylethane and/or 1-benzoyl-1-hydroxy-1-methylethane.

In accordance with the invention, the compounds of the formula I and the mixtures (blends) of compounds of the formula Ia with compounds of the formula II and/or III and/or IV can be used as photoinitiators for the photopolymerization of ethylenically unsaturated compounds and of mixtures which include such compounds. This use may also be practised in combination with other additives.

The invention therefore also provides photopolymerizable compositions comprising (a) at least one ethylenically unsaturated photopolymerizable compound and (b) as photoinitiator, at least one compound of the formula I or a photoinitiator mixture as described above, it being possible for the composition to contain not only component (b) but also other additives.

The unsaturated compounds may contain one or more olefinic double bonds. They may be of low molecular mass (monomeric) or of relatively high molecular mass (oligomeric). Examples of monomers containing a double bond are alkyl or hydroxyalkyl acrylates or methacrylates, for example, methyl, ethyl, butyl, 2-ethylhexyl- or 2-hydroxyethyl acrylate, isobornyl acrylate, or methyl or ethyl methacrylate. Silicone acrylates are also of interest. Further examples are acrylonitrile, acrylamide, methacrylamide, N-substitututed (meth)acryl-amides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol and of bisphenol-A,4,4'-bis(2-acryloyloxyethoxy) diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate and tris(2-acryloylethyl) isocyanurate.

Examples of relatively high molecular mass (oligomeric) polyunsaturated compounds are acrylicized epoxy resins, and polyethers, polyurethanes and polyesters which are acrylicized or contain vinyl ether groups or epoxy groups. Further examples of unsaturated oligomers are unsaturated polyester resins which are mostly prepared from maleic acid, phthalic acid and one or more diols and have molecular weights of from about 500 to 3000. In addition it is also possible to employ vinyl ether monomers and vinyl ether oligomers, and also maleate-terminated oligomers having polyester, polyurethane, polyether, polyvinyl ether and epoxy main chains. Combinations of oligomers which carry vinyl ether groups and of polymers as described in WO 90/01512 are particularly suitable. However, copolymers of vinyl ether and maleic acid functionalized monomers are also appropriate. Such unsaturated oligomers can also be referred to as prepolymers.

Examples of particularly suitable compounds are esters of ethylenically unsaturated carboxylic acids and polyols of polyepoxides, and polymers containing ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers containing (meth)acrylic groups in side chains, and mixtures of one or more such polymers.

Examples of unsaturated carboxylic acids are acrylic, methacrylic, crotonic, itaconic and cinnamic acid, and unsaturated fatty acids such as linolenic acid and oleic acid. Acrylic acid and methacrylic acid are preferred.

Suitable polyols are aromatic polyols and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the said polyols, especially on the aromatic polyols and epichlorohydrin. Other suitable polyols include polymers and copolymers which contain hydroxyl groups in the polymer chain or in side groups, for example polyvinyl alcohol and copolymers thereof, or hydroxyalkyl polymethacrylates or copolymers thereof. Further suitable polyols are oligoesters containing hydroxyl end groups.

Examples of aliphatic and cycloaliphatic polyols are alkylene diols, preferably with 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols with molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified by means of one or more unsaturated carboxylic acids, where the free hydroxyl groups in partial esters may be modified, for example etherified or esterified with other carboxylic acids.

Examples of esters are:

Trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethyacrylate, sorbitol pentaacrylate, sorbitol hexaacrylate, oligoester acrylates and methacrylates, glycerol di- and -triacrylate, 1,4-cyclohexane diacrylate, bisacrylates and bismethacrylates of polyethylene glycol of molecular weight from 200 to 1500, or mixtures thereof.

Further suitable components (a) are the amides of identical or different unsaturated carboxylic acids of aromatic, cycloaliphatic and aliphatic polyamines, preferably having 2 to 6, in particular 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylendiamine, bisphenylenediamine, di-β-aminoethyl ether, diethylenetriamine, triethylenetetramine, di(β-aminoethoxy)- or di(β-aminopropoxy)ethane. Further suitable polyamines are polymers and copolymers which may contain additional amino groups in the side chain, and oligoamides containing amino end groups. Examples of unsaturated amides of this kind are: methylenebisacrylamide, 1,6-hexamethylenebisacrylamide, diethylenetriaminetrismethacrylamide, bis(methacrylamidopropoxy)ethane, β-methacrylamidoethyl methacrylate, and N-[(β-hydroxyethoxy)ethyl]acrylamide.

Suitable unsaturated polyesters and polyamides are derived, for example, from maleic acid and diols or diamines. Some of the maleic acid may be replaced by other dicarboxylic acids. They can be employed together with ethylenically unsaturated comonomers, for example styrene. The polyesters and polyamides may also be derived from dicarboxylic acids and ethylenically unsaturated diols or diamines, especially from relatively long-chain compounds containing, for example, from 6 to 20 carbon atoms. Examples of polyurethanes are those built up from saturated or unsaturated diisocyanates and from unsaturated and/or saturated diols.

Polybutadiene and polyisoprene and copolymers thereof are known. Examples of suitable comonomers are: olefins such as ethylene, propene, butene, hexene, (meth)acrylates, acrylonitrile, styrene and vinyl chloride. Polymers containing (meth)acrylate groups in the side chain are also known. These may be, for example, products of the reaction of novolak-based epoxy resins with (meth)acrylic acid, homopolymers or copolymers of vinyl alcohol or hydroxyalkyl derivatives thereof which have been esterified using (meth)acrylic acid, or homopolymers and copolymers of (meth)acrylates which have been esterified using hydroxyalkyl (meth)acrylates.

The photopolymerizable compounds can be employed alone or in any desired mixtures. Preference is given to mixtures of polyol (meth)acrylates.

It is also possible to add binders to the novel compositions, which is particularly expedient if the photopolymerizable compounds are liquid or viscous substances. The amount of binder may be, for example, 5–95% by weight, preferably 10–90% by weight and, in particular, 40–90% by weight, based on the overall solids content. The binder is chosen depending on the field of use and on the properties required therefor, such as the facility for development in aqueous and organic solvent systems, adhesion to substrates, and sensitivity to oxygen.

Examples of suitable binders are polymers having a molecular weight of about 5000–2 000 000, preferably 10 000–1 000 000. Examples are homo- and copolymeric acrylates and methacrylates, for example copolymers of methyl methacrylate/ethyl acrylate/methacrylic acid, poly (alkyl methacrylate), poly(alkyl acrylates); cellulose esters and cellulose ethers, such as cellulose acetate, cellulose acetate butyrate, methylcellulose, ethylcellulose; polyvinylbutyral, polyvinylformal, cyclized rubber, polyether such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethyleneadipamide), and polyesters such as poly(ethylene glycol terephthalate) and poly(hexamethylene glycol succinate).

The unsaturated compounds can also be used in mixtures with non-photopolymerizable film-forming components. These may, for example, be physically drying polymers or solutions thereof in organic solvents, for example nitrocellulose or cellulose acetobutyrate. However, they can also be chemically curable or heat-curable resins, for example polyisocyanates, polyepoxides or melamine resins. The additional use of heat-curable resins is important for use in so-called hybrid systems, which are photopolymerized in a first step and are crosslinked by thermal aftertreatment in a second step.

The photopolymerizable mixtures may contain various additives in addition to the photoinitiator. Examples of these are thermal inhibitors, which are intended to prevent premature polymerization, examples being hydroquinone, hydroquinone derivatives, p-methoxyphenol, β-naphthol or sterically hindered phenols, such as 2,6-di(tert-butyl)-p-cresol. The shelf life in the dark can be increased, for example, by using copper compounds, such as copper naphthenate, copper stearate or copper octoate, phosphorus compounds, for example triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, such as N-diethylhydroxylamine. In order to keep out atmospheric oxygen during the polymerization, paraffin or similar wax-like substances can be added; these migrate to the surface on commencement of the polymerization because of their low solubility in the polymer, and form a transparent surface layer which prevents the ingress of air. It is likewise possible to apply an oxygen barrier layer. Light stabilizers which can be added are UV absorbers, for example those of the hydroxyphenylbenzotriazole, hydroxyphenylbenzophenone, oxalamide or hydroxyphenyl-s-triazine type. It is possible to use individual such compounds or mixtures thereof, with or without the use of sterically hindered amines (HALS).

Examples of such UV absorbers and light stabilizers are 1.2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl) benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3', 5'-di-tert-amyl-2'-hydroxyphenyl) benzotriazole, 2-(3',5'-bis(α,α-dimethylbenzyl)-2'-hydroxyphenyl)-benzotriazole, a mixture of 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$ where R=3'-tert-butyl-4'-hydroxy-5'-2H-benzotriazol-2-ylphenyl.

2.2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

3. Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl) resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl α-cyano-β,β-diphenylacrylate or isooctyl α-cyano-β,β-diphenylacrylate, methyl α-carbomethoxycinnamate, methyl α-cyano-β-methyl-p-methoxy-cinnamate or butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethylpiperidyl) sebacate, bis(2,2,6,6-tetramethylpiperidyl) succinate, bis(1,2,2,6,6-pentamethylpiperidyl) sebacate, bis(1,2,2,6,6-pentamethylpiperidyl) n-butyl 3,5-di-tert-butyl-4-hydroxybenzylmalonate, the condensate of 1-hydroxyethyl-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl) bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, the condensate of N,N'-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N, N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis (2,4-dimthylpheny)-1,3,5-triazine, 2-[2-hydroxy-4(2-hydroxy-3-octyoxypyloxy)-phenyl]-4,6bis (2,4-dimethylphenyl)-1,3,5,-triazine, 2-[4-4-dodecyl/tridecyloxy-(2-hydroxypropyl)oxy-2-hydroxyphenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl) pentaerythritol diphosphite, bis(2,4,6-tri-tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenzo[d,g]-1,3,2-dioxaphosphocin, 6-fluoro-2,4,8,10-tetra-tert-butyl-1 2-methyl-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

Consequently, the invention also provides photopolymerizable compositions comprising as photoinitiator at least one compound of the formula I, or a photoinitator mixture as described above, and a UV absorber from the class of the hydroxyphenyl-s-triazines and/or hydroxyphenylbenzotriazoles and/or sterically hindered amines based on 2,2,6,6-tetramethylpiperidines.

Preference is given to a composition comprising a photoinitiator mixture of compounds of the formulae Ia, especially bis(2,4,6-trimethylbenzoyl)phenylphosphine oxide, and compounds of the formula II, especially 1-benzoylcyclohexanol and 1-benzoyl-1-hydroxy-1-methylethane, and a mixture of 85% 4,6-di(2,4-dimethylphenyl)-2-[2-hydroxy-4-(mixture of dodecyloxy and tridecyloxy)(2-hydroxy)propyl-3-oxyphenyl]-1,3,5-triazine and 15% 1-methoxy-2-propanol as UV absorber.

To accelerate the photopolymerization it is possible to add amines, for example triethanolamine, N-methyldiethanolamine, ethyl p-dimethylaminobenzoate or Michler's ketone. The action of the amines can be intensified by the addition of aromatic ketones of the benzophenone type. If use is made of novel mixtures comprising compounds of the formula III, an improvement in the reactivity can be obtained through the addition of amines. Examples of amines which can be used as oxygen scavengers are substituted N,N-dialkylanilines as described in EP-A-339 841. Further accelerators, coinitiators and autoxidizers are thiols, thioethers, disulfides and phosphines, as are described, for example, in EP-A-438 123 and GB-A-2 180 358.

The photopolymerization can also be accelerated by the addition of photosensitizers, which shift or broaden the spectral sensitivity. These are, in particular, aromatic carbonyl compounds, such as benzophenone derivatives, thioxanthone derivatives, anthraquinone derivatives and 3-acylcoumarin derivatives, and also 3-(aroylmethylene) thiazolines, and also eosine, rhodamine and erythrosine dyes.

The curing procedure can be assisted, in particular, by compositions which are pigmented (for example with titanium dioxide), and also by adding a component which forms free radicals under thermal conditions, for example an azo compound such as 2,2'-azobis(4-methoxy-2,4-dimethylvaleronitrile), a triazene, a diazo sulfide, a pentazadiene or a peroxy compound, such as a hydroperoxide or peroxycarbonate, for example t-butyl hydroperoxide, as described in EP-A 245 639.

The novel compositions can also include a photoreducible dye, for example xanthene, benzoxanthene, benzothioxanthene, thiazine, pyronine, porphyrin or acridine dyes, and/or a trihalomethyl compound which can be cleaved by radiation. Similar compositions are described, for example, in EP-A-445 624.

Other conventional additives are—depending on the intended application—fluorescent whiteners, fillers, pigments, dyes, wetting agents or levelling assistants. Thick and pigmented coatings can suitably be cured by the addition of glass microbeads or powdered glass fibres, as described in U.S. Pat. No. 5,013,768, for example.

The invention also provides compositions comprising as component (a) at least one ethylenically unsaturated, photopolymerizable compound which is emulsified or dissolved in water.

Radiation-curable, aqueous prepolymer dispersions of this type are commercially available in numerous variations. This term is taken to mean a dispersion of water and at least one prepolymer dispersed therein. The concentration of water in these systems is, for example, from 5 to 80% by weight, in particular from 30 to 60% by weight. The radiation-curable prepolymer or prepolymer mixture is present, for example, in concentrations of from 95 to 20% by weight, in particular from 70 to 40% by weight. The total of the percentages indicated for water and prepolymers in these compositions is in each case 100, to which are added the auxiliaries and additives in various amounts depending on the intended application.

The radiation-curable, water-dispersed, film-forming prepolymers, which are frequently also dissolved, are, for aqueous prepolymer dispersions, monofunctional or polyfunctional ethylenically unsaturated prepolymers which are known per se, can be initiated by means of free radicals and contain, for example, from 0.01 to 1.0 mol of polymerizable double bonds per 100 g of prepolymer, and have a mean molecular weight of, for example, at least 400, in particular from 500 to 10,000. Depending on the intended application, however, prepolymers having higher molecular weights might also be suitable. For example, use is made of polyesters containing polymerizable C—C double bonds and having a maximum acid number of 10, polyethers containing polymerizable C—C double bonds, hydroxyl-containing products of the reaction of a polyepoxide containing at least two epoxide groups per molecule with at least one α,β-ethylenically unsaturated carboxylic acid, polyurethane (meth)acrylates, and α,β-ethylenically unsaturated acrylic copolymers containing acrylic radicals, as are described in EP-A-12 339. Mixtures of these prepolymers may also be used. Also suitable are the polymerizable prepolymers described in EP-A-33 896, which are thioether adducts of polymerizable prepolymers having a mean molecular weight of at least 600, a carboxyl group content of from 0.2 to 15% and a content of from 0.01 to 0.8 mol of polymerizable C—C double bonds per 100 g of prepolymer. Other suitable aqueous dispersions based on specific alkyl (meth)acrylate prepolymers are described in EP-A-41 125; suitable water-dispersible, radiation-curable prepolymers made from urethane acrylates are disclosed in DE-A-2 936 039. These radiation-curable, aqueous prepolymer dispersions may include, as further additives, dispersion assistants, emulsifiers, antioxidants, light stabilizers, dyes, pigments, fillers, for example talc, gypsum, silica, rutile, carbon black, zinc oxide and iron oxides, reaction accelerators, levelling agents, lubricants, wetting agents, thickeners, matting agents, defoamers and other assistants which are customary in coatings technology. Suitable dispersion assistants are water-soluble organic compounds of high molecular mass which contain polar groups, examples being polyvinyl alcohols, polyvinylpyrrolidone and cellulose ethers. Emulsifiers which can be used are nonionic emulsifiers and possibly also ionic emulsifiers.

The photopolymerizable compositions comprise the photoinitiator or the photoinitiator mixture (b) advantageously in an amount of from 0.05 to 15% by weight, preferably from 0.1 to 5% by weight, based on the composition.

Where the novel photoinitiators are employed in hybrid systems, use is made—in addition to the novel free-radical hardeners of cationic photoinitiators, for example benzoyl peroxide, aromatic sulfonium or iodonium salts, or cyclopentadienylarene iron(II) complex salts.

In certain cases it may be an advantage to use further initiators in addition to the novel compounds or photoinitiator mixtures. For example, phosphines or phosphonium salts or, for example, compounds of the formula

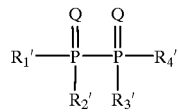

(described in , U.S. Pat. No. 5,436,280 or JP-A-Hei 6 263809) in which Q is S or O and $R_1'$, $R_2'$, $R_3'$ and $R_4'$ are, for example, alkyl, alkenyl or aryl, and phosphites can be used as additives.

The photopolymerizable compositions can be used for various purposes, for example as printing inks, as transparent coatings, as white paints, for example for wood or metal, as coating materials for substrates including paper, wood, metal and plastic, as daylight-curable coatings for marking buildings and roads, for photographic reproduction techniques, for holographic recording materials, for image recording processes or for the production of printing plates which can be developed using organic solvents or aqueous-alkaline media, for the production of masks for screen printing, as dental filling materials, as adhesives, as pressure-sensitive adhesives, as laminating resins, as etch resists or permanent resists, and as solder masks for electronic circuits, for the production of three-dimensional articles by bulk curing (UV curing in transparent moulds) or by the stereolithography process, as is described, for example in U.S. Pat. No. 4,575,330, for the preparation of composite materials (e.g. styrenic polyesters, which may, if appropriate, contain glass fibres and other auxiliaries) and other thick-layer compositions, for the coating or encapsulation of electronic components, or as coatings for optical fibres.

The novel compounds and photoinitiator mixtures can additionally be used as initiators for emulsion polymerizations, as initiators of a polymerization for the fixing of ordered states of liquid-crystalline monomers and oligomers, and as initiators for the fixing of dyes on organic materials.

In surface coatings, mixtures of a prepolymer with polyunsaturated monomers are often used which also include a monounsaturated monomer. The prepolymer here is primarily responsible for the properties of the coating film, and variation thereof allows the person skilled in the art to influence the properties of the cured film. The polyunsaturated monomer functions as a crosslinking agent which renders the coating film insoluble. The monounsaturated monomer acts as a reactive diluent by means of which the viscosity is reduced without the need to use a solvent.

Unsaturated polyester resins are usually used in two-component systems together with a monounsaturated monomer, preferably with styrene. For photoresists, specific single-component systems are often used, for example polymaleimides, polychalkones or polyimides, as are described in DE-A-2 308 830.

The novel compounds and mixtures may also be used, for example, in coating materials which are in organic solvents and/or water or are solvent-free.

The novel compounds and mixtures thereof can also be used as free-radical photoinitiators or photoinitiating systems for radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE-A-42 28 514 and in EP-A-636 669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using, for example, medium-pressure mercury lamps, metal halide lamps or xenon lamps. A particular advantage of the radiation-curable powder coatings over their heat-curable counterparts is that the flow time after melting of the powder particles can be delayed if desired in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiators, the powder coating formulations may also include UV absorbers. Appropriate examples are listed above in sections 1.-8.

The novel photocurable compositions are suitable, for example, as coating materials for substrates of all kinds, for example wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate a reproduced image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating. It is also possible to apply the photosensitive layer to a temporary, flexible support and then to coat the final substrate, for example a copper-clad circuit board, by transferring the layer via lamination.

The quantity applied (layer thickness) and the nature of the substrate (layer support) are dependent on the desired field of application. The range of layer thicknesses generally comprises value from about 0.1 $\mu$m to more than 100 $\mu$m.

The novel radiation-sensitive compositions find application as negative resists, having a very high sensitivity to light and being able to be developed in an aqueous alkaline medium without swelling. They are suitable as photoresists for electronics (electroplating resist, etch resist, solder resist), the production of printing plates, such as offset printing plates or screen printing formes and/or the production of dies, for use in chemical milling or as a microresist in the production of integrated circuits. The possible layer supports, and the processing conditions of the coated substrates, are just as varied. Substrates used for photographic information recording include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing forms are generally from about 0.5 $\mu$m to 10 $\mu$m, while for printed circuits they are from 0.4 $\mu$m to about 2 $\mu$m.

Following the coating of the substrates, the solvent is removed, generally by drying, to leave a coat of the photoresist on the substrate.

The term "imagewise" exposure includes both exposure through a photomask comprising a predetermined pattern, for example a slide, exposure by means of a laser beam, which for example is moved under computer control over the surface of the coated substrate and in this way produces an image, and irradiation with computer-controlled electron beams.

Following the imagewise exposure of the material and prior to development, it may be advantageous to carry out thermal treatment for a short time. In this case only the exposed sections are thermally cured. The temperatures employed are generally 50–150° C., preferably 8–130° C.; the period of thermal treatment is in general between 0.25 and 10 minutes.

The photocurable composition may additionally be used in a process for producing printing plates or photoresists as is described, for example, in DE-A-40 13 358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents. Photocuring is of great importance for printing inks, since the drying time of the binder is a critical factor for the production rate of graphic products, and should be in the order of fractions of seconds. UV-curable inks are particularly important for screen printing.

As already mentioned above, the novel mixtures are also highly suitable for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent.

Another field where photocuring is employed is the coating of metals, in the case, for example, of the coating of metal plates and tubes, cans or bottle caps, and photocuring of polymer coatings, for example of floor or wall coverings based on PVC.

Examples of the photocuring of paper coatings are the colourless varnishing of labels, record sleeves and book covers.

Also of interest is the use of the novel compounds for curing shaped articles made from composite compositions. The composite composition consists of a self-supporting matrix material, for example a glass fibre fabric, or alternatively, for example, plant fibres [cf.K.-P. Mieck, T. Reussmann in Kunststoffe 85 (1995), 366–370], which is impregnated with the photocuring formulation. Shaped parts comprising composite compositions, when produced using the novel compounds, attain a high level of mechanical stability and resistance. The novel compounds can also be employed as photocuring agents in moulding, impregnating and coating compositions as are described, for example, in EP-A-7086. Examples of such compositions are gel coat resins, which are subject to stringent requirements regarding curing activity and yellowing resistance, and fibre-reinforced mouldings, for example light-diffusing panels which are planar or have lengthwise or crosswise corrugation. Techniques for producing such mouldings, such as hand lay-up, spray lay-up, centrifugal casting or filament winding, are described, for example, by P. H.

Selden in "Glasfaserverstärkte Kunststoffe", page 610, Springer Verlag Berlin-Heidelberg-New York 1967.

Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc. Curing is carried out using medium-pressure mercury lamps as are conventional in UV curing. However, there is also particular interest in less intense lamps, for example of the type TL 40W/03 or TL40W/05. The intensity of these lamps corresponds approximately to that of sunlight. It is also possible to use direct sunlight for curing. A further advantage is that the composite composition can be removed from the light source in a partly cured, plastic state and can be shaped, with full curing taking place subsequently.

The use of photocurable compositions for imaging techniques and for the optical production of information carriers is also important. In such applications, as already described above, the layer (wet or dry) applied to the support is irradiated through a photomask with UV or visible light, and the unexposed areas of the layer are removed by treatment with a solvent (=developer). Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce printed electronic circuits and photoresists.

The photosensitivity of the novel compositions extends in general from the UV (about 200 nm) region about 600 nm and therefore spans a very broad range. Suitable radiation is present, for example, in sunlight or light from artificial light sources. Consequently, a large number of very different types of light source are employed. Both point sources and arrays ("lamp carpets") are suitable. Examples are carbon arc lamps, xenon arc lamps, medium-, high- and low-pressure mercury lamps, possibly doped with metal halide (metal-halogen lamps), microwave-stimulated metal vapour lamps, excimer lamps, superactinic fluorescent tubes, fluorescent lamps, argon incandescent lamps, electronic flashlamps, photographic floodlamps, electron beams and X-rays, produced by means of synchrotrons or laser plasma. The distance between the lamp and the substrate to be exposed in accordance with the invention may vary depending on the intended application and the type and output of the lamp, and may be, for example, from 2 cm to 150 cm. Laser light sources, for example excimer lasers, are especially suitable, such as krypton F lasers for exposure at 248 nm. Lasers in the visible region can also be employed. In this case, the high sensitivity of the novel materials are very advantageous. By this method it is possible to produce printed circuits in the electronics industry, lithographic offset printing plates or relief printing plates, and also photographic image-recording materials.

The invention additionally provides for the use of the above-described composition for preparing coating materials, printing inks, printing plates, dental compositions, resist materials, and as image recording material, especially for holographic recordings.

The invention additionally provides a coated substrate which is coated on at least one surface with a composition as described above, and provides a process for the photographic production of relief images, in which a coated substrate is subjected to imagewise exposure and then the unexposed portions are removed with a solvent. Imagewise exposure in this case can take place through a mask or else using a controlled laser (without a mask).

The invention thus also provides a process for the photopolymerization of compounds containing ethylenically unsaturated double bonds, which comprises irradiating a composition as described above, with light in the range from 200 to 600 nm.

The compounds of the formulae I and Ia are photosensitive solids, which are generally yellow, and which are soluble, for example, in esters, aromatic compounds, alcohols and chlorinated hydrocarbons.

The novel photoinitiator mixtures (blends) are of good solubility in the substrate that is to be cured. In this context, the solubility of the blends in the substrate to be cured is generally better than the solubility of the individual components. In the blend, one component acts as a solubilizer for the others.

When carrying out curing with the novel blends, an optimum ratio can be obtained between the curing of the surface of the substrate and its through-curing.

The photoinitiator mixtures are reactive, and low yellowing values can be achieved in the course of curing.

The examples which follow illustrate the invention in more detail. Parts and percentages, as in the remainder of the description and in the claims, are by weight unless indicated otherwise.

EXAMPLE 1

Preparation of bis (2,4,6-trimethylbenzoyl)-4-methylphenylphosphine oxide

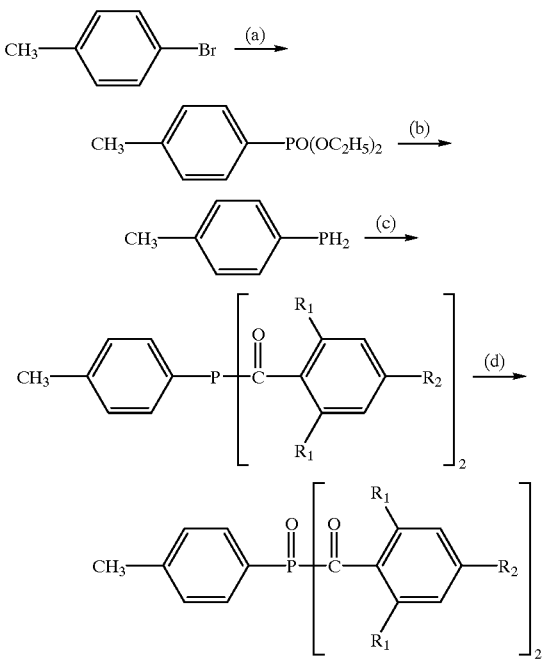

(a) 4-Methylphenyldiethylphosphonate

In a Hickmann apparatus, 51.3 g of 4-bromotoluene are heated with 3.9 g of nickel(II) chloride to 160° C. 74.8 g of triethyl phosphite are added dropwise over the course of one hour. The reaction mixture is then heated at 160° C. for 2 hours. Subsequently, 22 g of ethyl bromide are distilled off. Distillation at 90° C./$10^{-2}$ mbar gives 38.6 g of 4-methylphenyidiethylphosphonate.

(b) 4-Methylphenylphosphine 8.23 g of lithium aluminium hydride are placed in 180 ml of dry diethyl ether, and 16.43 g of 4-methylphenyidiethylphosphonate are added at −10° C. The suspension is stirred at room temperature for 18 hours and then washed carefully with 8 ml of water at 0° C. and 5° C., and hydrolysed with 8 g of 15% NaOH solution and 24 ml of water, to give a bulky white precipitate. This precipitate is filtered off under argon, and washed with 50 ml of ether, and the solvent is distilled off under argon, to give 9.0 g of 4-methylphenylphosphine which is used without further purification for the preparation of the next stage.

(c) Bis(2,4,6-trimethylbenzoyl)-4-methylphenylphosphine

A solution of 16.2 g of diisopropylamine in 50 ml of tetrahydrofuran (THF) is cooled to −10° C. 100 ml of butyllithium in hexane (1.6 M) are added dropwise. Then, at −40° C., first 9.0 g of 4-methylphenylphosphine and, subsequently, a solution of 29.22 g of 2,4,6-trimethylbenzoyl chloride in 150 ml of THF are added. The solution is stirred for 1.5 hours and then the solvent is removed under reduced pressure, to give 28.0 g of bis(2,4,6-trimethylbenzoyl)-4-methylphenylphosphine as a yellow powder.

(d) Bis(2,4,6-trimethylbenzoyl)-4-methylphenylphosphine oxide 28.0 g of bis(2,4,6-trimethylbenzoyl)-4-methylphenylphosphine are dissolved in 100 ml of toluene and the solution is heated to 50° C. 8.2 g of 30% hydrogen peroxide are added dropwise over the course of one hour. The reaction mixture is then allowed to cool to room temperature, and the phases which develop are separated. The organic phase is washed with 30 ml of water, 30 ml of 10% sodium bicarbonate solution and water until neutral, then is dried over magnesium sulfate, filtered and concentrated in vacuo, to give 24.5 g of a yellow oil. Column chromatography and recrystallization from petroleum ether give 12. g of the title product as yellow crystals with a melting point of 151–152° C.

Elemental analysis:

| calc. | C: | 74.98% | found: | C: | 74.90% |
|---|---|---|---|---|---|
|  | H: | 6.76% |  | H: | 6.75% |

EXAMPLES 2–9

The compounds of Example 2 to 9 are obtained by following the method described in Example 1 and using the appropriately substituted starting materials. The compounds and their physical data are given in Table 1 below.

TABLE 1

| Example | $R_1$ | $R_2$ | $R_3$ | $R_5$ | $R_6$ | $R_7$ | mp [° C.] | Elemental analysis [%] calculated [%] found C | H |
|---|---|---|---|---|---|---|---|---|---|
| 1 | $CH_3$ | $CH_3$ | H | $CH_3$ | H | H | 152 | 74.90 / 74.98 | 6.75 / 6.76 |
| 2 | $CH_3$ | $CH_3$ | $CH_3$ | H | H | H | 132 | 74.81 / 74.98 | 6.80 / 6.76 |
| 3 | $CH_3$ | $CH_3$ | $CH_3$ | $CH_3$ | H | $CH_3$ | 163 | 75.47 / 75.63 | 7.30 / 7.22 |
| 4 | $CH_3$ | $CH_3$ | $CH(CH_3)_2$ | H | $CH(CH_3)_2$ | H | 160 | 76.17 / 76.47 | 7.92 / 7.82 |
| 5 | $CH_3$ | $CH_3$ | $CH_3$ | $C(CH_3)_3$ | H | $CH_3$ | 146 | 76.58 / 76.47 | 6.03 / 7.82 |
| 6 | $CH_3$ | $CH_2CH(CH_3)_2$ | H | H | H | H | resin | 76.22 / 76.47 | 8.02 / 7.82 |
| 7 | $CH_3$ | H | H | H | H | H | 93 | 73.61 / 73.81 | 6.02 / 5.94 |
| 8 | $CH_3$ | $CH_3$ | H | H | H | H | 132 | 74.63 / 74.67 * | 6.50 / 6.52 |
| 9 | $CH_3$ | $CH_3$ | $CH_3$ | H | $CH_3$ | H | 122 | 75.04 / 75.32 ** | 6.97 / 7.00 |

*The shift δ in the $^{31}$P—NMR spectrum is 7.50 ppm.
**The shift δ in the $^{31}$P—NMR spectrum is 14.95 ppm.

EXAMPLE 10
Preparation and Curing of a Transparent Coating A UV-curable clearcoat is prepared by mixing 99.5 parts of ®Roskydal 502 (=66% unsaturated polyester resin and 34% styrene; Bayer)

0.5 part of ®Byk 300 (=levelling assistant, Byk-Mallinckrodt).

Two parts of a mixture of 95% 1-benzoyl-1-hydroxy-1-methylethane and 5% of the photoinitiator from Example 8 are incorporated into this formulation. The coating material is applied to a chipboard panel using a doctor blade with a 200 μm gap and is then cured.

Curing is conducted by passing the sample, on a conveyor belt moving at a speed of 5 m/min, underneath two medium-pressure mercury lamps of the 120 W/cm Fusion H type (Fusion Systems, USA) and 80 W/cm Hanovia type (Canrad-Hanovia, USA). The König pendulum hardness (DIN 53157) of the smearproof coating is 52 seconds.

EXAMPLE 11
Preparation and Curing of a White Paint

A UV-curable white paint is prepared by mixing 67.5 parts of ®Ebecryl 830 (Polyester acrylate from UCB, Belgium)

5.0 parts of 1,6-hexanediol diacrylate 2.5 parts of trimethylolpropane triacrylate and 25.0 parts of ®R-TC2 (rutile titanium dioxide, from Tioxide)

3 parts of a photoinitiator mixture of 75% 1-benzoyl-1-hydroxy-1-methylethane and 25% of of the photoinitiator from Example 8 are incorporated into this paint formulation. The paint is applied to a coil-coated aluminium panel using a doctor blade with a 100 μm gap, and is exposed on a conveyor belt to an 80 W/cm medium-pressure mercury lamp (Canrad-Hanovia, USA). The maximum belt speed at which a smearproof and through-cured coat is obtained is a measure of the reactivity of the photoinitiator mixture. A coat cured at a belt speed of 3 m/min has a König pendulum hardness (DIN 53157) of 159 seconds.

EXAMPLE 12
Preparation and Curing of a White Paint

Similarly, in each case 3 parts of a photoinitiator mixture of 75% 1-benzoyl-1-hydroxy-cyclohexane and 25% of the photoinitators from Examples 2, 4 and 7 were tested in the formulation described in Example 11. The corresponding white-paint coats are likewise cured at a belt speed of 15 m/min.

EXAMPLE 13
Preparation and Curing of a Highly Pigmented White Paint

A UV-curable white paint is prepared by mixing 45 parts of ®Ebecryl 830

3 parts of 1,6-hexanediol diacrylate 2 parts of trimethylolpropane triacrylate 50 parts of ®R-TC2 (rutile titanium dioxide)

4 parts of a photoinitiator mixture of 75% 1-benzoyl-1-hydroxycyclohexane and 25% of the photoinitiator from Example 8 are incorporated into this paint formulation. The paint is applied to coil-coated aluminium panels using a doctor blade with a 150 μm gap and is cured on a conveyor belt under two 80 W/cm medium-pressure mercury lamps (Aetek, USA). At a belt speed of 10 m/min, a smearproof and through-cured coat is obtained whose König pendulum hardness (DIN 53157) is 85 seconds. 4 parts of a photoinitiator mixture of 75% 1-benzoyl-1-hydroxycyclohexane and 25% of the photoinitiator from Example 3 likewise give a smearproof surface and through-cured coat at a belt speed of 10 m/min, with a pendulum hardness of 79 seconds.

EXAMPLE 14
Curing of a Laminar Composite

A formulation is prepared from 99 parts of ®Vestopal X7231 (unsaturated polyester from Hüls, Germany) and 1 part of a photoinitiator mixture of 75% benzyl dimethyl ketal and 25% of the photointiator from Example 8

A lamina of 4 layers of a glass fibre mat (chopped strand material) and the above formulation are covered with a transparent Mylar film and subjected to firm compression. This assembly is then irradiated under 5 lamps of type TL40W/03 (Philips) at a distance of 15 cm for 10 minutes. A stable composite layer is obtained which has a Shore hardness D (in accordance with DIN 53505; determined with a hardness tester from Otto Wolpert Werke, Ludwigshafen, Germany) of 65.

EXAMPLE 15
Preparation and Curing of an Amino-containing Clearcoat 2 parts of a photoinitiator mixture of 45% benzophenone, 45% 1-benzoyl-1-hydroxy-cyclohexane and 10% of the photoinitiator from Example 8 are mixed with 98 parts of an amino-containing polyether acrylate (®Laromer PO84 F, BASF). The coating material is applied to chipboard panels using a doctor blade with a 100 μm gap and is cured at a belt speed of 10 m/min using two 80 W/cm medium-pressure mercury lamps (Aetek, USA). The smearproof coat has a König pendulum hardness (DIN 53157) of 65 seconds.

EXAMPLE 16
Preparation and Curing of a Powder Coating

A UV-curable powder coating is prepared from 56.0 parts of ®ZA 3125 (DSM, Holland)

1 1.0 parts of ®ZA 3126 (DSM, Holland)

33.0 parts of ®R-TC2 (rutile titanium dioxide)

1.0 part of ®Resiflow PV5 (E.H. Worlee, Germany)

0.5 part of ®Worlee Add 900 (E.H. Worlee, Germany)

3.0 parts of a photoinitiator mixture of 75% 4(2-hydroxyethoxy)benzoyl-1-hydroxy-1-methylethane and 25% of the photoinitiator from Example 8

All of the components are mixed in an extruder at 80° C., to give a homogeneous white paint. After cooling, the solid mass is ground and sieved. The powder with a particle size of <90 μm is applied in a film thickness of 60–90 μm to an aluminium panel using an electrostatic spray method. The coated panel is heated at 125° C. in an oven for 3 minutes. During this period, the powder melts and a homogeneous film is formed. The film is irradiated while still hot, at a belt speed of 7.5 m/min, under two 80 W/cm medium-pressure mercury lamps. After irradiation for 30 minutes, a König pendulum hardness of 105 seconds is measured.

EXAMPLE 17
A Pastel-coloured Paint is Prepared by Mixing 75.5 parts of Ebecryl® 830 (polyester acrylate oligomer)

9.0 parts of 1,6-hexanediol diacrylate (HDODA)

4.5 parts of trimethylolpropane triacrylate (TMPTA)

To this paint there are added 3% (3 parts) of a photoinitiator mixture of 75% benzyl dimethyl ketal and 25% of of the photoinitiator from Example 1. A paint film of 100 μm is applied to a wooden panel and is exposed, at a belt speed of 3 m/min, under two 80 W/cm medium-pressure mercury lamps (Aetek, USA). A smearproof and through-cured coat is obtained whose König pendulum hardness (DIN 53157) is 115 seconds.

EXAMPLE 18

A Yellow Paint is Prepared From 83.0 parts of Ebecryl® 830 (polyester acrylate oligomer)

9.5 parts of 1,6-hexanediol diacrylate (HDODA)

4.0 parts of trimethylolpropane triacrylate (TMPTA)

3.0 parts of Irgazin® Gelb GLTN (yellow pigment)

3 parts of the photoinitiator mixture from Example 17 are added to this paint. The paint is applied as described in Example 17 and is exposed, at a belt speed of 3 m/min, with an 80 W/cm medium-pressure mercury lamp (Canrad-Hanovia, USA). The pendulum hardness of the smearproof and through-cured coat is 142 seconds.

EXAMPLE 19

UV Stabilization of a Clearcoat

A clearcoat is prepared by mixing 99.5 parts of Roskydal® 502 (=66% unsaturated polyester with 34% styrene, BAYER), and 0.5 part of Byk® 300 (levelling assistant, Byk-Mallinckrodt)

A liquid 3-component mixture is prepared by heating a photoinitiator mixture of 75% 1-benzoyl-1-hydroxycyclohexane and 25% of the photoinitiator from Example 1 to 50° C. and adding the same amount by weight of a mixture of 85% 4,6-di(2,4-dimethylphenyl)-2-[2-hydroxy-4-(mixture of dodecyloxy and tridecyloxy)(2-hydroxy)propyl-3-oxyphenyl]-1,3,5-triazine and 15% 1-methoxy-2-propanol. 4 parts of this liquid mixture are incorporated into the clearcoat. Coats are applied to wood (pale substrate) using a doctor blade with a 150 µm gap, and are exposed at a belt speed of 3 m/min, using two 80 W/cm medium-pressure mercury lamps. The pendulum hardnesses (PH) and yellowness indices (YI) (according to ASTMD 1925) are measured directly after curing and after 4 hours of subsequent exposure under TL 20W/05 fluorescent lamps (Philips).

The sample with the liquid 3-component mixture can be cured readily and gives an adequate photoprotective action (UV stabilization), as shown by the data in Table 2.

TABLE 2

| Additives | after curing | | 4 hours TL 20W/05 | |
|---|---|---|---|---|
| | PH | YI | PH | YI |
| 4 parts of liquid 3-component mixture | 88 | 9.8 | 134 | 9.5 |

EXAMPLE 20

Incorporation of a Liquid Mixture into an Aqueous Pigmented Formulation

A pigmented aqueous formulation is prepared by mixing the following components:

50 parts of Roskydal® 850 W (unsaturated polyester, BAYER)

50 parts of Laromer® PE 55 W (emulsion of a polyester acrylate in water, BASF)

10 parts of titanium dioxide R-TC2 (rutile type)

20 parts of water

The photoinitiator mixture of 75% 1-benzoyl-1-hydroxycyclohexane and 25% of the photoinitiator from Example 1 is liquefied at 50° C., and 3 parts thereof are incorporated at room temperature into the above formulation, with stirring. Coats 150 µm thick are applied to wood, dried at 80° C. for 4 minutes and then exposed at 3 m/min under two 80 W/cm medium-pressure mercury lamps. The coating with the liquefied photoinitiator mixture gives a pendulum hardness of 50 seconds, a yellowness index of 4.3 and gloss values (at measurement angles of 20° and 60°) of 75/87.

What is claimed is:

1. A compound of formula I

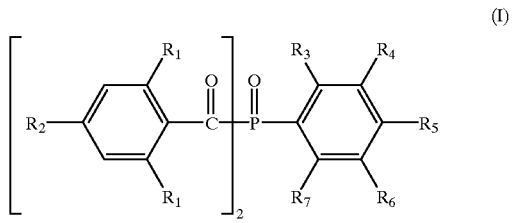

in which $R_1$ is $C_1$–$C_4$alkyl, $R_2$ is hydrogen, methyl or $C_1$–$C_4$alkoxy, $R_3$, $R_5$ and $R_7$ independently of one another are hydrogen, halogen, $C_1$–$C_{20}$alkyl, cyclopentyl, cyclohexyl, $C_2$–$C_{12}$alkenyl, or are phenyl-substituted $C_1$–$C_4$alkyl, or are phenyl which is unsubstituted or mono- or di-substituted by $C_1$–$C_4$alkyl and/or $C_1$–$C_4$alkoxy, and $R_4$ and $R_6$ independently of one another are hydrogen, halogen, cyclopentyl, cyclohexyl, $C_2$–$C_{12}$alkenyl, or are phenyl-substituted $C_1$–$C_4$alkyl, or are phenyl which is unsubstituted or mono- or di-substituted by $C_1$–$C_4$alkyl and/or $C_1$–$C_4$alkoxy, and with the proviso that at least one of the radicals $R_3$, $R_4$, $R_5$, $R_6$ and $R_7$ is other than hydrogen, and that, if $R_1$ and $R_2$ are methyl, $R_5$ is not methyl.

2. A compound according to claim 1, in which $R_3$, $R_5$ and $R_7$ are hydrogen, $C_1$–$C_8$-alkyl, phenyl, allyl, benzyl, cyclohexyl or chlorine and $R_4$ and $R_6$ are hydrogen, phenyl, allyl, benzyl, cyclohexyl or chlorine.

3. A compound according to claim 1, in which $R_3$ and $R_5$ are hydrogen, $C_1$–$C_4$alkyl or phenyl and $R_4$ is hydrogen or phenyl.

4. A compound according to claim 1, in which $R_1$ is methyl.

5. A compound according to claim 1, in which $R_1$ and $R_2$ are the same.

* * * * *